(12) United States Patent
Jolly

(10) Patent No.: US 8,128,551 B2
(45) Date of Patent: Mar. 6, 2012

(54) REMOTE SENSING AND ACTUATION OF FLUID OF INNER EAR

(75) Inventor: Claude Jolly, Innsbruck (AT)

(73) Assignee: MED-EL Elektromedizinische Geraete GmbH, Innsbruck (AT)

(*) Notice: Subject to any disclaimer, the term of this patent is extended or adjusted under 35 U.S.C. 154(b) by 739 days.

(21) Appl. No.: 11/778,165

(22) Filed: Jul. 16, 2007

(65) Prior Publication Data

US 2008/0064918 A1 Mar. 13, 2008

Related U.S. Application Data

(60) Provisional application No. 60/831,351, filed on Jul. 17, 2006.

(51) Int. Cl.
*H04R 25/00* (2006.01)
(52) U.S. Cl. .......................................... 600/25; 607/57
(58) Field of Classification Search .................... 600/25; 623/10; 607/55–57
See application file for complete search history.

(56) References Cited

U.S. PATENT DOCUMENTS

| | | | | |
|---|---|---|---|---|
| 5,176,620 A | * | 1/1993 | Gilman | 600/25 |
| 5,411,467 A | * | 5/1995 | Hortmann et al. | 600/25 |
| 6,259,951 B1 | | 7/2001 | Kuzma et al. | 607/57 |
| 6,629,922 B1 | | 10/2003 | Puria et al. | 600/25 |
| 2003/0097121 A1 | * | 5/2003 | Jolly et al. | 604/891.1 |

FOREIGN PATENT DOCUMENTS

| | | |
|---|---|---|
| DE | 391806 C1 | 9/1990 |
| WO | WO03/034960 | 5/2003 |
| WO | WO2004/024212 | 3/2004 |

OTHER PUBLICATIONS

PCT, International Search Report ; PCT/US2007/073572.

* cited by examiner

*Primary Examiner* — Charles A Marmor, II
*Assistant Examiner* — Carrie R Dorna
(74) *Attorney, Agent, or Firm* — Sunstein Kann Murphy & Timbers LLP

(57) ABSTRACT

A system for communicating with the inner ear is described. An acoustic transducer converts between electrical energy and mechanical energy. An inner ear catheter has a distal end in vibratory communication with the fluid of the inner ear, a proximal end in vibratory communication with the acoustic transducer, and a lumen filled with a catheter fluid for coupling vibratory signals between the distal end and the proximal end.

26 Claims, 5 Drawing Sheets

REMOTE SENSING AND ACTUATION OF FLUID OF INNER EAR

This application claims priority from U.S. Provisional Patent Application 60/831,351, filed Jul. 17, 2006, the contents of which are incorporated herein by reference.

FIELD OF THE INVENTION

The present invention relates to implantable devices, and more particularly to implantable devices for mechanical and electrical stimulation and fluid delivery for the inner ear.

BACKGROUND ART

FIG. 1 shows the anatomy of a normal human ear. A normal ear transmits sounds through the outer ear 101 to the eardrum 102, which moves the three bones of the middle ear 103, which in turn excites the cochlea 104. The cochlea, or inner ear, 104 includes an upper channel known as the scala vestibuli 105 and a lower channel known as the scala tympani 106, which are connected by the cochlear duct 107. In response to received sounds, the stapes, a bone of the middle ear 103, transmits vibrations via the fenestra ovalis, (oval window) 114, to the perilymph (inner ear fluid) of the cochlea 104. Vibrations in the inner ear fluid are dissipated out of the fenestra rotunda (round window) 115. As a result, the hair cells of the organ of Corti are excited to initiate chemical-electric pulses that are transmitted to the cochlear nerve 113, and ultimately to the brain.

Some patients may have partially or completely impaired hearing for reasons including: long term exposure to environmental noise, congenital defects, damage due to disease or illness, use of certain medications such as aminoglycosides, or physical trauma. Hearing impairment may be of the conductive, sensory neural, or combination types.

There are several types of middle- and inner-ear implants that can restore a sense of partial or full hearing. Implants often include various electromagnetic transducers that may function as an actuator, a sensor, and/or a switch. An example of an implant with an electromagnetic actuator is a middle ear implant which mechanically drives the ossicular chain, the three bones of the middle ear that mechanically connect the eardrum to the oval window. Another example of an implant with an electromagnetic actuator is a middle ear implant that mechanically drives the tympanic membrane.

Another type of implant relies on direct electrical stimulation of the nerves in the inner ear. For example, intra-cochlear electrodes can restore some sense of hearing by direct electrical stimulation of the neural tissue in proximity of an electrode contact. These electrodes are typically located on the end of an electrode carrier that is threaded into the cochlea. The electrodes are connected to, for example, an implanted signal processor which communicates with an external signal processor that produces an electrical stimulation signal for the implanted electrodes to stimulate the cochlear nerve.

In order to treat certain inner ear disorders, it is often necessary to deliver therapeutic agents directly into the cochlea. An example of a system for delivering therapeutic agents to the inner ear is a catheter that is inserted into the cochlea via the round window. The end of the catheter might be infused with a therapeutic agent that is released into the inner ear fluid. The catheter might also include a fluid reservoir with a solution of the therapeutic agent that is in fluid communication with the inner ear fluid. Alternatively, the catheter might include a fluid filled lumen containing a solution of the therapeutic agent that is in fluid communication with the inner ear fluid. Delivery of therapeutic agents to the cochlea is described further in U.S. patent application Ser. No. 11/374,505, filed Mar. 13, 2006, the contents of which are incorporated herein by reference.

SUMMARY OF THE INVENTION

In an embodiment of the present invention, a system for communicating with the inner ear includes a acoustic transducer that converts between electrical energy and mechanical energy. An inner ear catheter has a distal end in vibratory communication with the fluid of the inner ear, a proximal end in vibratory communication with the acoustic transducer, and a lumen filled with a catheter fluid for coupling vibratory signals between the distal end and the proximal end.

In further such embodiments, there may also be a housing chamber enclosing the acoustic transducer and filled with a housing fluid in vibratory communication with the proximal end of the inner ear catheter. The acoustic transducer may be, for example, a floating mass transducer.

The distal end of the lumen may be in fluid communication with the fluid of the inner ear, the proximal end of the lumen may be in fluid communication with the housing fluid, and the housing may further include a fluid port for receiving therapeutic fluid for delivery to the inner ear.

In an embodiment, a housing chamber may be filled with a housing fluid in vibratory communication with the proximal end of the catheter and may include an outer housing membrane in vibratory communication with the housing fluid. The acoustic transducer may be located outside the housing chamber in vibratory communication with the housing membrane.

In such an embodiment, the distal end of the lumen may be in fluid communication with the fluid of the inner ear, the proximal end of the lumen may be in fluid communication with the housing fluid, and the housing may further include a fluid port for receiving therapeutic fluid for delivery to the inner ear.

Embodiments may include a microphone coupled to the housing membrane for sensing fluid mechanics associated with the auditory structures. The distal end of the lumen may be in fluid communication with the fluid of the inner ear. The lumen may include a fluid port for receiving therapeutic fluid for delivery to the inner ear. The distal end of the lumen may include a distal membrane in vibratory communication with the fluid of the inner ear.

The acoustic transducer may be adapted for use in the outer ear, the middle ear, or the inner ear of a user and/or may be adapted to be secured to the skull of a user. The distal end of the inner ear catheter may be adapted for use in the scala tympani of a user.

Any of the foregoing embodiments may also include an electronics module for producing an electrical stimulation signal for the inner ear, and an electrode array at the distal end of the inner ear catheter and in electrical communication with the electronics module for stimulating neural tissue of the inner ear with the electrical stimulation signal.

BRIEF DESCRIPTION OF THE DRAWINGS

The foregoing features of the invention will be more readily understood by reference to the following detailed description, taken with reference to the accompanying drawings

DETAILED DESCRIPTION OF SPECIFIC EMBODIMENTS

In the past, inner ear sensing devices and amplifiers have been brought into the closest feasible proximity to the structures of the inner ear. But this approach has many problems and is difficult to implement in practice. Embodiments of the present invention dispose the device structures within the user in more spacious and accessible locations not directly adjacent to the inner rear by using a catheter to establish fluid communication between the inner ear and the system devices. The catheter can be filled with a vibration transmitting liquid, for example, by a port and/or septum membrane. The distal end of the catheter penetrates the inner ear and the proximal end couples to an acoustic transducer. Enclosing the fluid within the catheter isolates it from the fluid of the inner ear to avoid leaks and prevent bacterial contamination while providing convenient mechanical access to the inner ear. The catheter may include a semi-permeable membrane at the distal end to provide pharmacological access by use of therapeutic drugs adapted to migrate across the membrane into the fluid of the inner ear. In some embodiments, the proximal end of the catheter may also be coupled to a self-sealing semi-permeable septum membrane that allows the therapeutic drugs to be introduced in the catheter fluid. For example, the proximal end membrane may be located in the middle ear or mastoid cavity for actuation or sensing of the catheter fluid. In some embodiments, the membranes may also usefully be coupled to a microphone which senses the fluid mechanics associated with the auditory structures of the middle and/or inner ear.

Thus, embodiments of the present invention provide a safe and convenient leak proof and bacterial resistant interface between an implanted prosthetic system and the fluid of the inner ear.

Figure 1:
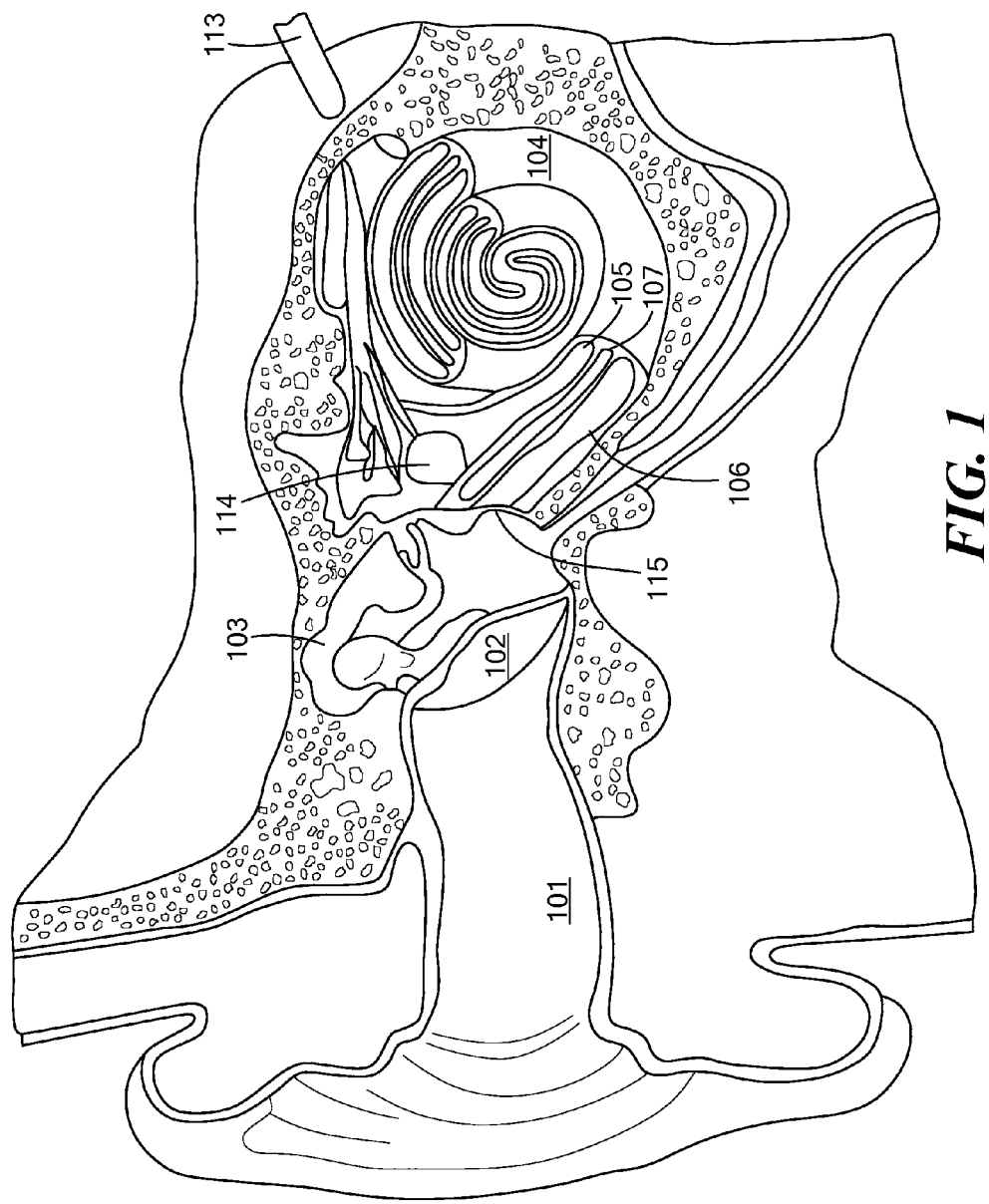
FIG. 1 shows the structure of the normal human ear.
Figure 2B:
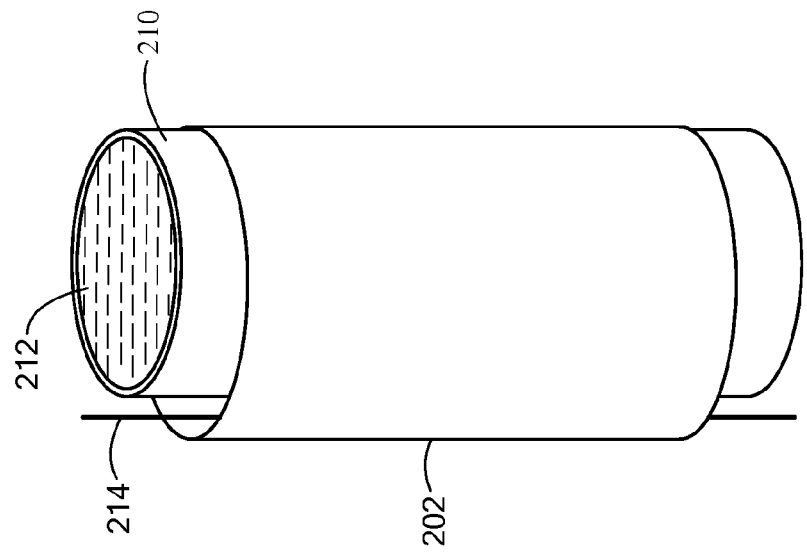
FIG. 2B is a cut-away illustration of a catheter of the present invention.
Figure 2A:
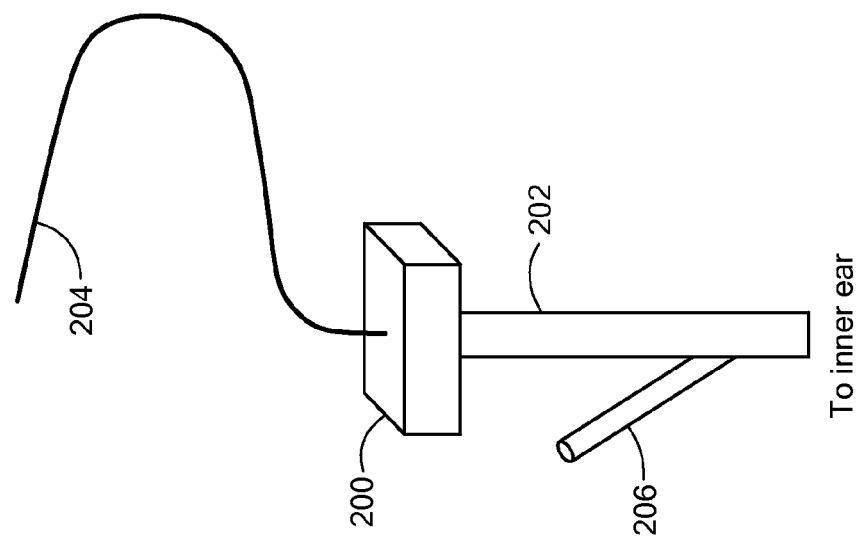
FIG. 2A is a graphical illustration of an embodiment of the present invention.

FIG. 2A is a graphical illustration of one embodiment of the invention showing a transducer-catheter arrangement. FIG. 2B is a cut-away cross-section of a portion of an inner ear catheter. In this embodiment, an acoustic transducer 200 is connected to the proximal end of an inner ear catheter 202. Wiring 204 may connect the acoustic transducer 200 to external circuitry. A fluid port 206 provides access to a catheter lumen 210 within the inner ear catheter 202. Inner ear catheter 202 can also include an electrode wire 214 that runs along the length of the catheter. Acoustic transducer 200 converts electrical energy into mechanical vibrations, and vice versa. For example, acoustic transducer 200 may produce vibrations in the human auditory range. Catheter lumen 210 is filled with a catheter fluid 212 (for example via septum port 206), which can transmit vibrations that are generated by the acoustic transducer 200 to the fluid of the inner ear. The acoustic transducer 200 is connected to the proximal end of the inner ear catheter 202 such that vibrations generated by the acoustic transducer 200 are transmitted into the catheter fluid 212. There is cooperation between the acoustic transducer 200, catheter lumen 210, and catheter fluid 212 such that a sufficient and appropriate amount of mechanical energy is generated by the acoustic transducer 200 and is transmitted by the catheter fluid 212 to the distal end of the catheter and into the inner ear fluid to be detected as sound by the inner ear. Alternatively, fluid movement generated within the inner ear by stapes movement may be transmitted through the catheter fluid 212 and detected by a sensitive membrane (e.g., a microphone diaphragm) associated with the acoustic transducer 200.

The catheter fluid 212 may be an artificial perilymph, or a physiological saline when the catheter lumen 210 is open to the fluid of the inner ear. If the distal end of the inner ear catheter 202 is to be placed in the scala media, then the catheter fluid 212 may usefully be an artificial endolymph. The catheter fluid 212 may be any liquid that facilitates or emphasizes mechanical energy transmission. The inner ear catheter 202 may be at least partially in the form of a channel through a cochlear implant electrode. Or the inner ear catheter 202 may be a separate catheter in parallel with a cochlear implant electrode. The inner ear catheter 202 may be made of an incompressible material to optimize transmission through the fluid 212 with minimal loss of energy. The volume of the catheter fluid 212 may usefully be minimized in order to maximize transmission of mechanical movements in the catheter fluid between the distal and proximal ends of the inner ear catheter 200.

The catheter lumen 210 may be open ended to the inner ear fluid, or it may be at least partially closed by a sensitive membrane such as a bacterial filter. The membrane may also prevent protein transport from the inner ear fluid through the catheter 210, and inhibit other diffusion processes. The membrane may be self-sealing and/or semi-porous to allow semi-permeable access to therapeutic drugs.

Figure 3:
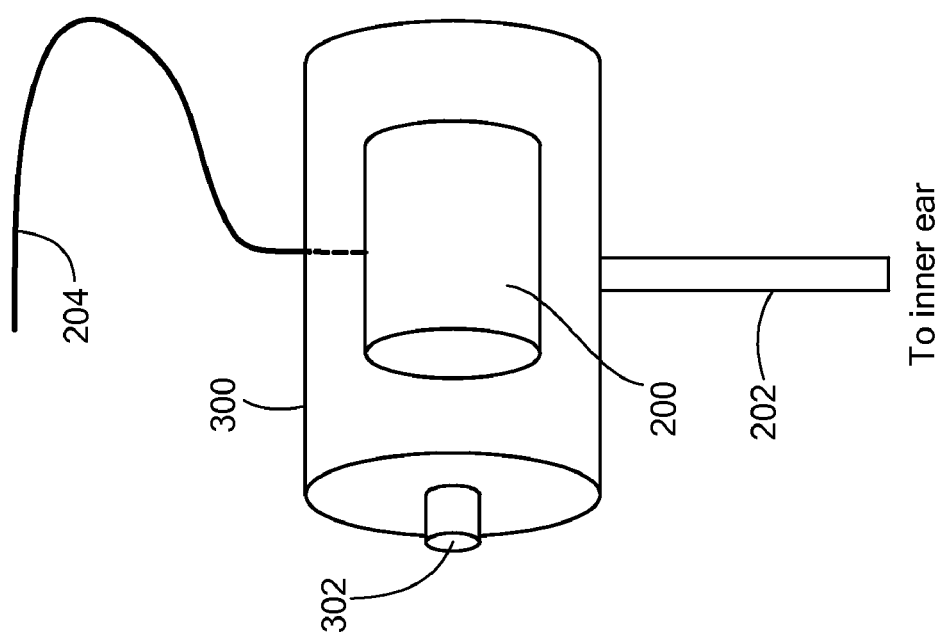
FIG. 3 is a graphical illustration showing a transducer enclosed in a housing chamber.

FIG. 3 shows another transducer arrangement in which acoustic transducer 200 is inside a housing chamber 300 that is filled with a fluid, and disposed such that vibrations generated by transducer 200 are transmitted to the chamber fluid. A septum port 302 with septum can be used for access to the fluid in housing chamber 300. The septum port 302 allows the housing chamber 300 and inner ear catheter 202 to be filled with a liquid of chosen composition. One challenge is to be able to fill the inner ear catheter 202 with a catheter liquid for optimal coupling between the acoustic transducer 200 and the fluid of the inner ear, and also providing an effective seal between the middle ear and the inner ear. Inner ear catheter 202 connects to housing chamber 300 so that mechanical vibrations generated by the acoustic transducer 200 will be transmitted through the chamber fluid to the catheter fluid 212. The fluid in the housing chamber 300 may be in fluid communication with the catheter fluid 212. Vibrations generated by the acoustic transducer 200 are transmitted through the catheter fluid 212 to the inner ear fluid. In this arrangement, the acoustic transducer 200 may be, for example, a floating mass transducer such as a vibrant FMT.

Figure 4:
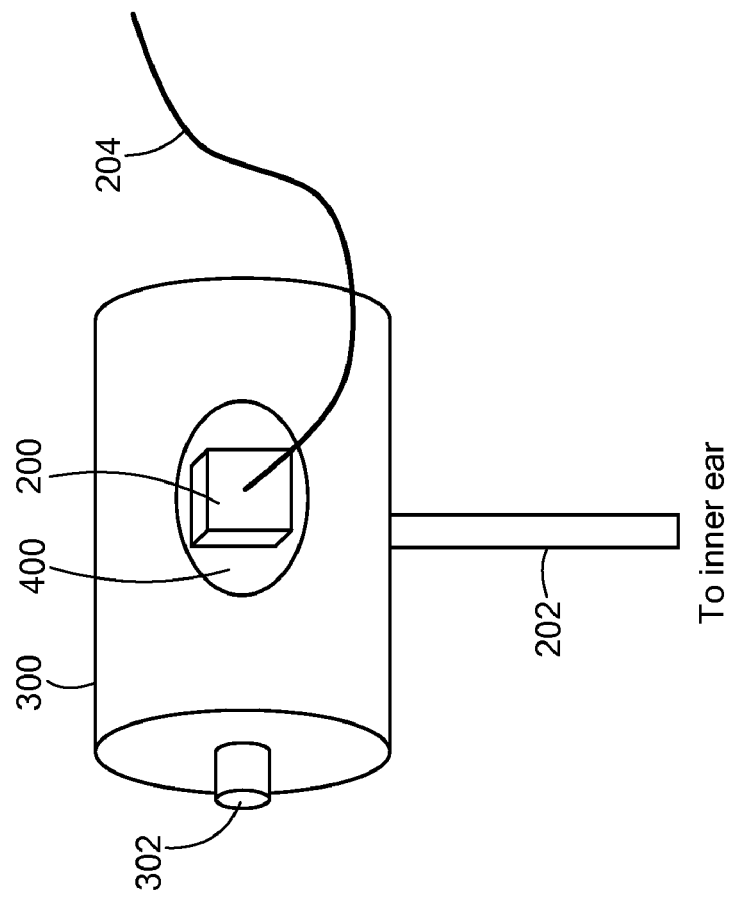
FIG. 4 is a graphical illustration showing a housing chamber having an external membrane, with the transducer in contact with the membrane.

FIG. 4 shows another transducer arrangement also involving a housing chamber 300. As in the embodiment of FIG. 3, inner ear catheter 202 connects to the housing chamber 300 so that mechanical vibrations will be transmitted through the chamber fluid to the catheter fluid 212. A septum port 302 can be used to fill the inner ear catheter 202 with the catheter fluid 212 and to provide access to the fluid in the housing chamber 300 through the port septum 302 The fluid in housing chamber 300 may be in fluid communication with the catheter fluid 212. In this embodiment, housing chamber 300 includes a housing membrane 400 through which vibrations can be transmitted to the chamber fluid (FIG. 4). Acoustic transducer 200 is external to the housing chamber 300, and is arranged and mounted with respect to the housing membrane 400 so that mechanical vibrations generated by the acoustic transducer 200 will be transmitted through the housing membrane 400 via the chamber fluid to the catheter fluid 212. These vibrations are then transmitted via the catheter fluid 212 through the distal end of the catheter to the inner ear fluid.

Figure 5:
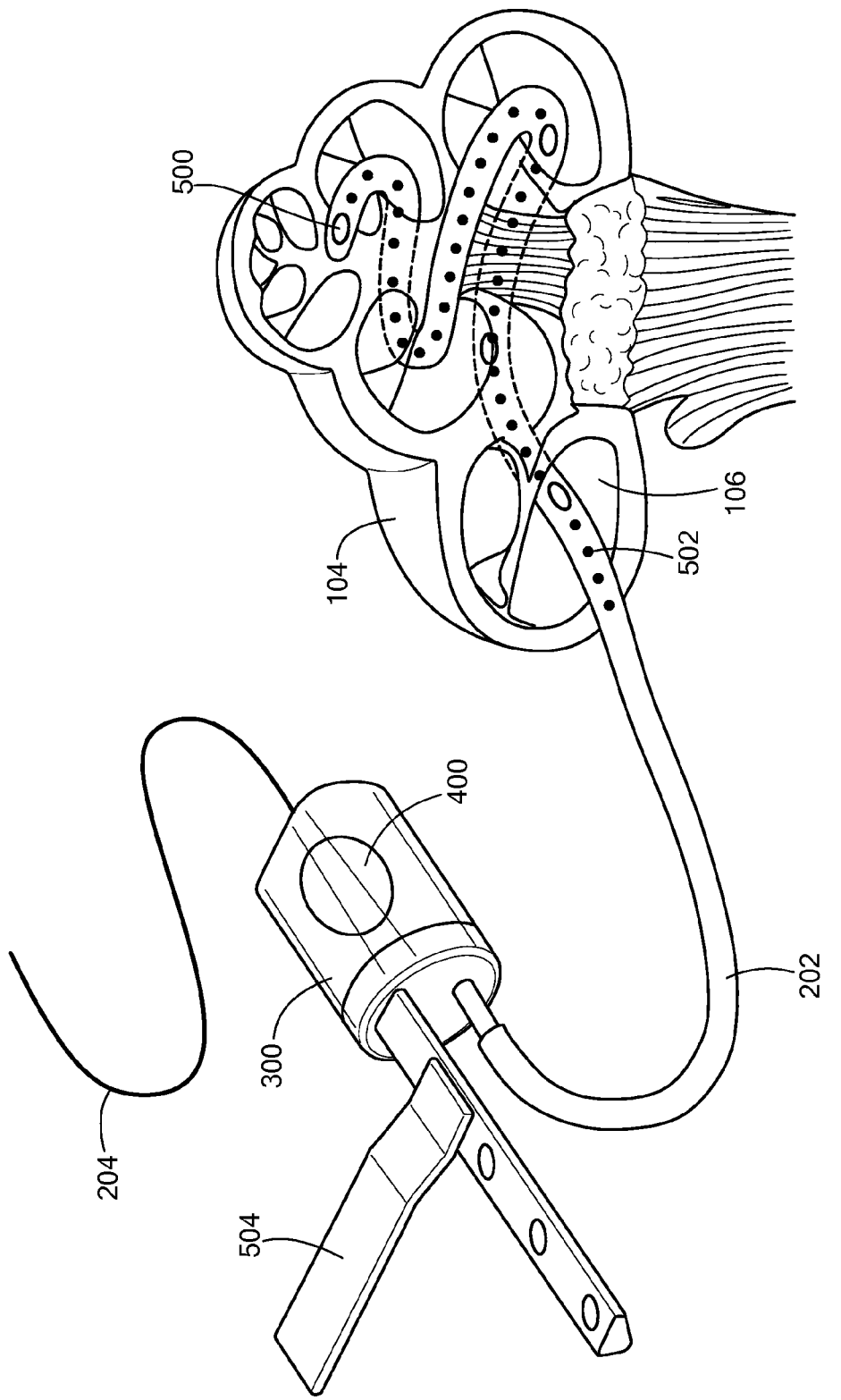
FIG. 5 is a pictorial illustration of an embodiment of the present invention showing a catheter threaded into the cochlea.

FIG. 5 is a pictorial illustration of a general embodiment of the present invention showing the inner ear catheter threaded into the cochlea 104 of a patient user. In this embodiment, the acoustic transducer 200 can be situated inside the housing chamber 300 as in the embodiment of FIG. 3. The acoustic transducer 200 can also be external to the housing chamber 300 and mounted against the housing membrane 400 as in the embodiment of FIG. 4. The housing membrane 400 can also be used, for example, to monitor the output of the acoustic transducer 200 when it is situated inside the housing chamber 300. The housing membrane 400 can also be of a selectively porous material such that therapeutic agents may be introduced into the housing fluid for delivery via the catheter fluid 212 to the inner ear. A mounting bracket 504 is shown that can be used to mount the acoustic transducer 200 to another assembly, or, in another configuration, directly to the bone (such as the skull) or other structures in the ear. In the embodiment shown, the inner ear catheter 202 also includes catheter membranes 500 and an electrode array 502. The catheter membranes 500 transmit the vibrations of the acoustic transducer 200 from the catheter fluid 212 to the inner ear fluid. In other embodiments, the catheter membranes 500 might be open ports or selectively porous membranes that allow therapeutic agents within the catheter fluid 212 to be delivered to the inner ear fluid. The electrode array 502 is connected to an electrode wire 214 and is used for electrical stimulation of the neural tissue of the inner ear. In such an arrangement, the electrode wire 214 may be connected to an implanted audio processor under the skin of a user near the outer ear.

Figure 6:
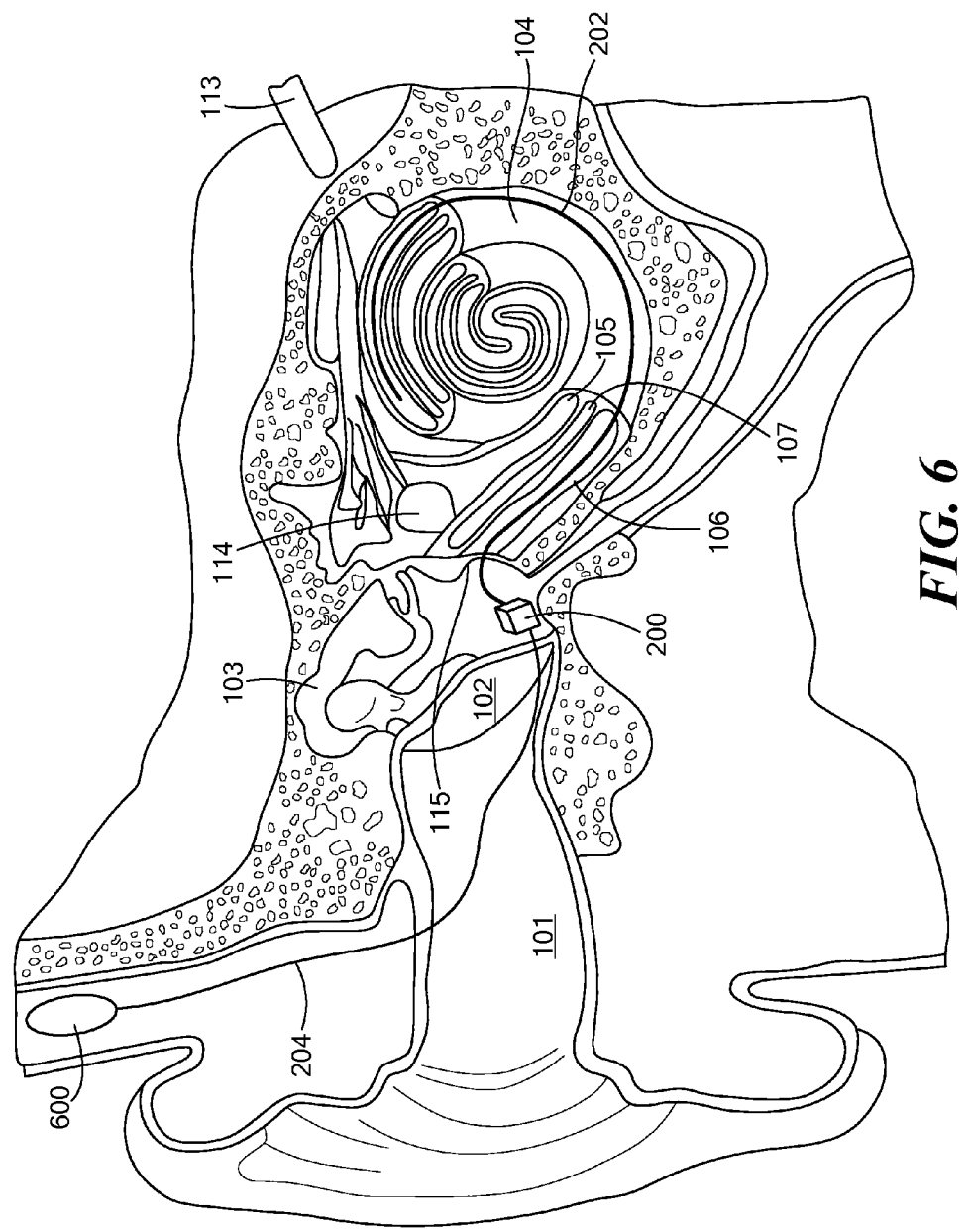
FIG. 6 shows the structure of the normal human ear with an embodiment of the present invention implanted in the cochlea.

FIG. 6 shows the structure of an ear along with an embodiment of the present invention implanted in the cochlea. The inner ear catheter 202 is threaded into the scala tympani 106 of the cochlea 104 via the round window 115. The acoustic transducer 200 is shown within the middle ear. Wiring 204 can be used to connect the acoustic transducer 200 and the electrode array 502 to other circuitry. For example, the electrode array 502 may be connected via the wiring 204 to an implanted audio processor 600 located under the skin near the outer ear. An audio processor 600 receives an audio signal and produces an electrical stimulation signal that is transmitted to the electrode array 502 via the wiring 204 for electrical stimulation of the neural tissue of the inner ear. The audio processor 600 contains electronic components for accepting an audio input from an audio source. In various embodiments, the audio processor 600 will accept analog signals, digital signals, or both. The audio input may be, but is not limited to, an analog or digital output from a microphone, telephone, television, stereo system, mp3 player, radio receiver, or computer. The audio input may be accepted via wired or wireless connection.

While the inventive system has been particularly shown and described, it is not intended to be exhaustive nor to limit the invention to the embodiments disclosed. It will be apparent to those skilled in the art that modifications can be made to the present invention without departing from the scope and spirit thereof. For example, while the embodiments shown have generally described a system to transmit vibrations produced by a transducer to the inner ear, the transducer can also be used to detect vibrations in the inner ear fluid via the catheter fluid. While the embodiments shown include wire for connecting various components, the wire is optional. This connection may be wireless, or the components may be optional. It is intended that the scope of the invention be defined by the claims appended hereto and their equivalents.

What is claimed is:

1. A system for communicating with the inner ear, comprising:
    an acoustic transducer for converting between electrical energy and mechanical energy; and
    an inner ear catheter having:
        i. a distal end adapted to be in vibratory communication with the fluid of the inner ear,
        ii. a proximal end adapted to be in vibratory communication with the acoustic transducer,
        iii. a lumen filled with a catheter fluid for coupling vibratory signals between the distal end and the proximal end; and
    a housing chamber enclosing the acoustic transducer and filled with a housing fluid that surrounds the acoustic transducer and is in vibratory communication with the proximal end of the inner ear catheter, wherein the housing chamber further comprises a fluid port for receiving therapeutic fluid for delivery to the inner ear.

2. The system of claim 1, wherein the acoustic transducer is a floating mass transducer.

3. The system of claim 1, wherein the proximal end of the lumen is adapted to be in fluid communication with the housing fluid.

4. The system of claim 1, wherein the housing chamber includes an outer housing membrane in vibratory communication with the housing fluid.

5. The system of claim 4, wherein the distal end of the lumen is adapted to be in fluid communication with the fluid of the inner ear, the proximal end of the lumen is adapted to be in fluid communication with the housing fluid.

6. The system of claim 4, further comprising:
    a microphone coupled to the housing membrane for sensing fluid mechanics associated with the auditory structures.

7. The system of claim 1, wherein the distal end of the lumen is adapted to be in fluid communication with the fluid of the inner ear.

8. The system of claim 7, wherein the lumen further comprises a fluid port for receiving therapeutic fluid for delivery to the inner ear.

9. The system of claim 1, wherein the distal end of the lumen includes a distal membrane adapted to be in vibratory communication with the fluid of the inner ear.

10. The system of claim 1, wherein the acoustic transducer is adapted for use in the middle ear of a user.

11. The system of claim 1, wherein the acoustic transducer is adapted for use in the outer ear of a user.

12. The system of claim 1, wherein the acoustic transducer is adapted to be secured to the skull of a user.

13. The system of claim 1, wherein the distal end of the inner ear catheter is adapted for use in the scala tympani of a user.

14. A system for communicating with the inner ear, comprising:
    an acoustic transducer for converting between electrical energy and a mechanical stimulation signal;
    an electronics module for producing an electrical stimulation signal for the inner ear;

an inner ear catheter having:
  i. a distal end adapted to be in fluid communication with the fluid of the inner ear,
  ii. a proximal end adapted to be in vibratory communication with the acoustic transducer, and
  iii. a lumen filled with a catheter fluid for coupling vibratory signals between the distal end and the proximal end and allowing fluid exchange between the catheter fluid and the fluid of the inner ear;

an electrode array at the distal end of the inner ear catheter and in electrical communication with the electronics module for stimulating neural tissue of the inner ear with the electrical stimulation signal; and a housing chamber enclosing the acoustic transducer and filled with a housing fluid that surrounds the acoustic transducer and is in vibratory communication with the proximal end of the inner ear catheter, wherein the housing chamber further comprises a fluid port for receiving therapeutic fluid for delivery to the inner ear.

15. The system of claim 14, wherein the transducer is a floating mass transducer.

16. The system of claim 14, wherein the proximal end of the lumen is adapted to be in fluid communication with the housing fluid.

17. The system of claim 14, wherein the housing chamber includes an outer housing membrane in vibratory communication with the housing fluid.

18. The system of claim 17, wherein the distal end of the lumen is adapted to be in fluid communication with the fluid of the inner ear, the proximal end of the lumen is adapted to be in fluid communication with the housing fluid.

19. The system of claim 17, further comprising:
  microphone coupled to the housing membrane for sensing fluid mechanics associated with the auditory structures.

20. The system of claim 17, wherein the distal end of the lumen is adapted to be in fluid communication with the fluid of the inner ear.

21. The system of claim 20, wherein the lumen further comprises a fluid port for receiving therapeutic fluid for delivery to the inner ear.

22. The system of claim 14, wherein the distal end of the lumen includes a distal membrane adapted to be in vibratory communication with the fluid of the inner ear.

23. The system of claim 14, wherein the acoustic transducer is adapted for use in the middle ear of a user.

24. The system of claim 14, wherein the acoustic transducer is adapted for use in the outer ear of a user.

25. The system of claim 14, wherein the acoustic transducer is adapted to be secured to the skull of a user.

26. The system of claim 14, wherein the distal end of the inner ear catheter is adapted for use in the scala tympani of a user.

* * * * *